United States Patent [19]
Guggenheim et al.

[11] Patent Number: 5,057,283
[45] Date of Patent: Oct. 15, 1991

[54] AUTOMATIC APPARATUS FOR CLEANING DENTISTRY HAND-PIECES OR TURBINES

[75] Inventors: Bernhard Guggenheim, Erlenbach, Switzerland; Michel Seigneurin, Bruthiers, France; Bernard Lacour; Jean-Paul Jacoulet, both of Besancon, France

[73] Assignee: Micro-Mega S.A., Besancon, France

[21] Appl. No.: 223,904

[22] Filed: Jul. 25, 1988

[30] Foreign Application Priority Data

Jul. 24, 1987 [FR] France ................ 87 10654

[51] Int. Cl.⁵ ............ B08B 3/02; B08B 3/04
[52] U.S. Cl. ................. 422/116; 472/6; 472/292; 472/295
[58] Field of Search ........... 433/103, 104, 131; 422/112, 113, 116, 26, 27, 28, 33, 37, 292, 295, 6; 134/22.12, 12, 18, 75, 79, 95, 102, 148, 138, 141, 104.1, 166 C, 168

[56] References Cited

U.S. PATENT DOCUMENTS 4,752,444 6/1988 Bowen et al. .............. 422/28

FOREIGN PATENT DOCUMENTS 3239549 4/1984 Fed. Rep. of Germany.

Primary Examiner—David L. Lacey
Assistant Examiner—Thomas E. Daley
Attorney, Agent, or Firm—Robert E. Burns; Emmanuel J. Lobato

[57] ABSTRACT

Automatic apparatus for cleaning dental handpieces and turbines is in the form of a housing having a compartment with hinged door. Standard motor noses project down from the top of the compartment to receive handpieces or turbines to be cleaned. Cleaning fluids, namely water, a disinfectant and oil are supplied sequentially to the motor noses while internal shafts of the motor noses are rotated by a set of pinions to drive the handpieces or turbines while the fluids are passed through them. The hinged door has an inflatable tube seal.

8 Claims, 2 Drawing Sheets

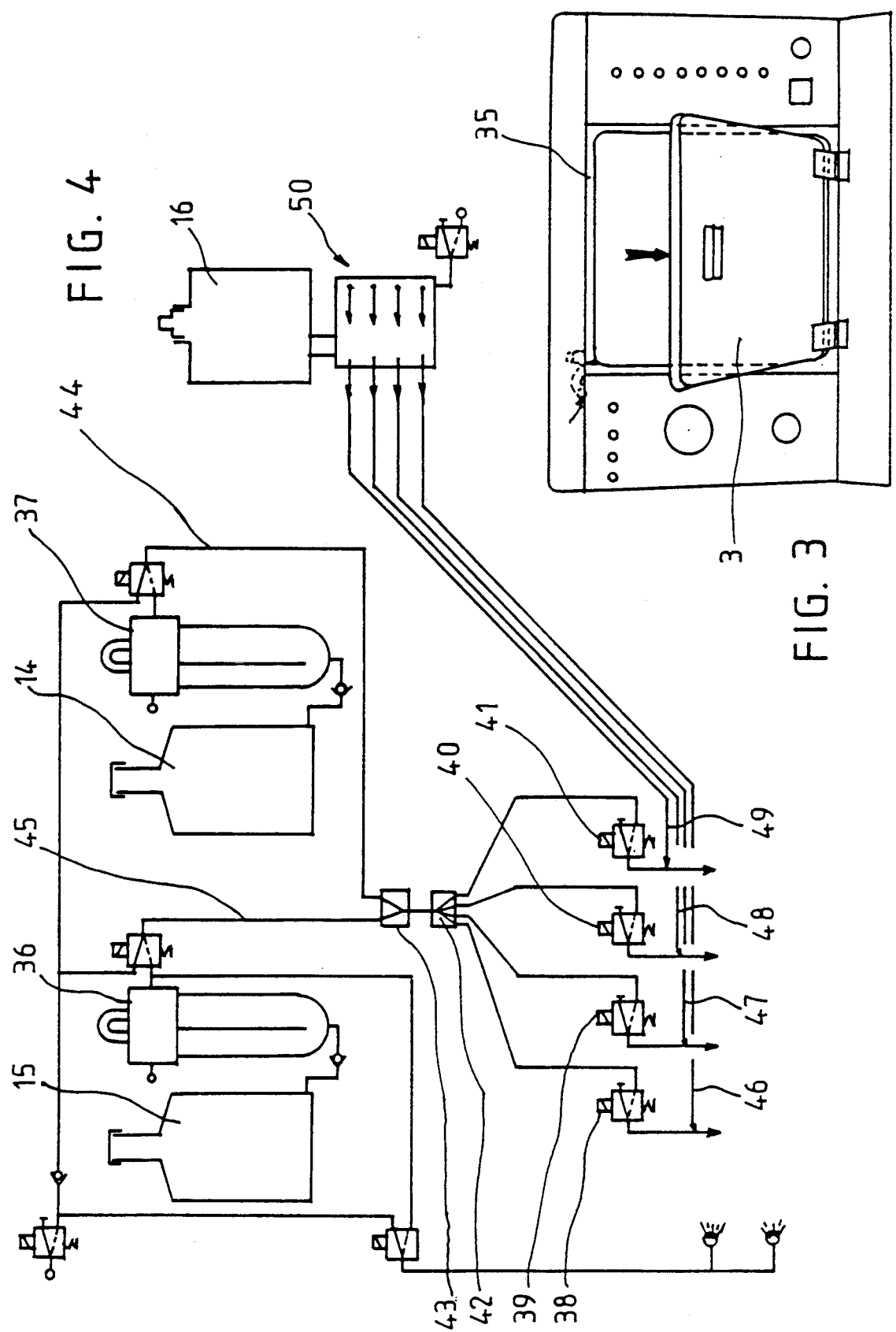

AUTOMATIC APPARATUS FOR CLEANING DENTISTRY HAND-PIECES OR TURBINES

The present invention relates to an automatic apparatus for cleaning one or more dentistry handpieces or turbines.

A dental surgeon must systematically clean, lubricate and sterilize at least once a day the handpieces which he uses.

At the present time these different operations are carried out manually with the aid of various instruments, such as for example aerosol sprays and the like. These operations are tedious and certain dentists therefore do not attend to them with the necessary frequency or thoroughness.

In this regard it should be noted that each handpiece must be cleaned separately, which consequently increases the time taken.

An automatic device has already been proposed in the Patent Application DE-OS 3 239 549 filed in the Federal Republic of Germany and published before examination. However, the device described is very makeshift and in fact works by suction (vacuum), which leads to very unreliable results where cleaning is concerned.

The present invention seeks to obviate these disadvantages by providing an automatic apparatus which permits the complete cleaning and the disinfection of one or more dentistry handpieces or turbines in such a manner as to present them ready for use.

According to the invention this result is obtained with an apparatus of the type referred to, which is characterized in that it comprises at least one standard dental motor nose which is provided with its drive means and on which the handpiece or handpieces to be cleaned are mounted, said nose or noses being connected to fluid reservoirs containing respectively water, a disinfectant and oil, which fluids can be passed in sequence for adjustable times and in adjustable amounts through the nose or noses and then through the handpiece or handpieces mounted thereon, the internal shafts of the handpiece or handpieces being rotationally driven by the nose or noses.

It is advantageous for the apparatus to work with compressed air, the air being delivered in succession by a system of solenoid valves into each of the fluid reservoirs so that these fluids are expelled from the respective reservoir and injected into the handpiece or handpieces, or the turbine, via the nose on which these parts are mounted.

The apparatus according to the invention will preferably be provided with a plurality of noses, for example three for handpieces and one for a turbine, which corresponds to the average equipment of a dental surgeon. In a manner known per se the noses each contain a shaft with its driver, each of these shafts being driven rotationally, according to the invention, by a pinion, all the pinions meshing with one another and a single drive pinion driving the whole arrangement and being driven in rotation, for example, by an air motor.

Numerous safety features are provided on the apparatus, such as for example:
visual indication of the fluid levels in the reservoirs;
operating safety with the aid of a door closing the chamber containing the parts to be cleaned;
closure valves on the noses to close them when they are not in use.

The invention will be better understood with the aid of the following description of a preferred embodiment, which is given by way of non-limitative example and with reference to the accompanying drawings, in which:

FIG. 3 shows a device for sealing the door of the apparatus, and

FIG. 4 shows the pneumatic diagram of the apparatus.

The basic principle consists in automatically cleaning one or more handpieces or turbines. A description will be given below of an apparatus constructed for three handpieces and one turbine, but it should be understood that this is in no way limitative.

According to the invention, a plurality of fluids are passed in succession into the interior of the parts to be cleaned, while the inner shafts rotate, these fluids being, for example, by way of indication:

water for a period of 18 to 100 seconds;
disinfectant liquid for a period of 18 to 100 seconds;
drying air for a period of 18 to 100 seconds;
lubricating oil for a period of 27 to 50 seconds.

At the end of this cycle the parts will have been cleaned, dried, disinfected, and lubricated and will be ready for use.

Figure 1:
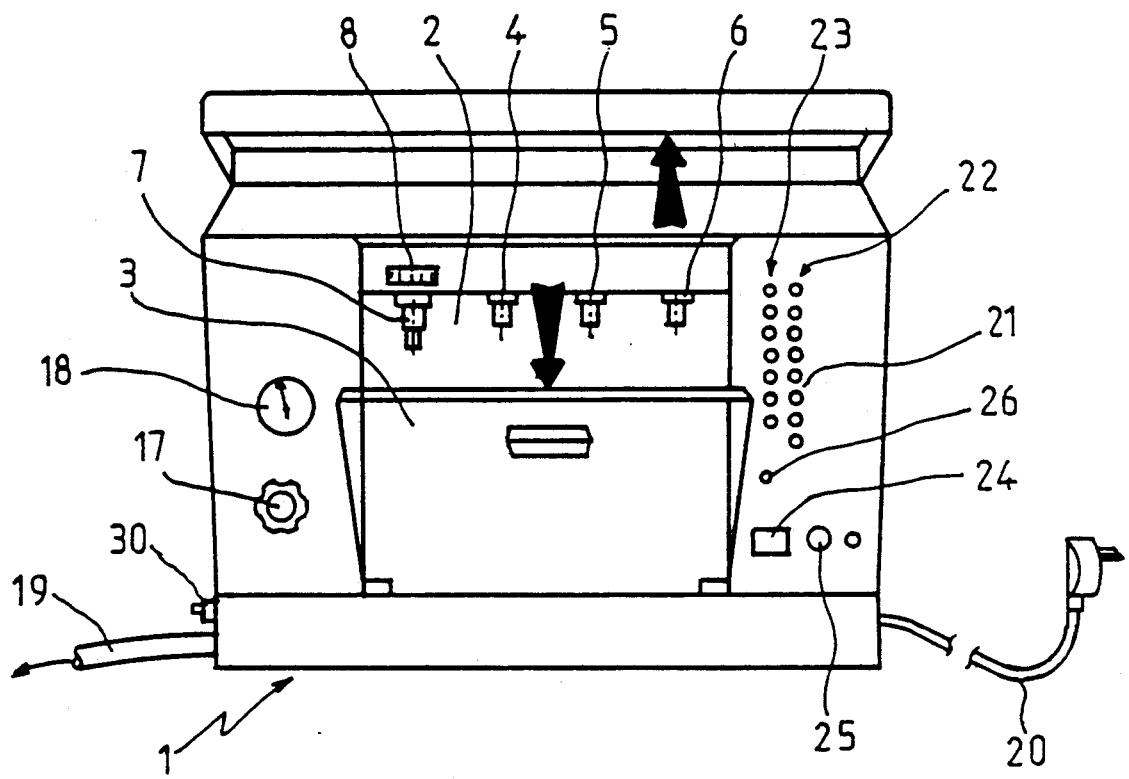
FIG. 1 is a front view of the apparatus according to the invention.

Reference will now be made to FIG. 1.

The apparatus according to the invention is in the form of a box 1 defining in its interior a chamber 2 closed at the front by a door 3 hinged, for example horizontally, on the box 1.

At the top the interior of this chamber contains three standard dental motor noses 4, 5, 6 on which the same number of handpieces (not shown) can be mounted in conventional manner. A fourth nose 7 can be provided to support a turbine.

The couplings are all known per se and will not be described in detail. The noses carrying the turbines may be of various types, known per se, depending on the air and spray inlet and outlet arrangement.

The turbine nose 7 can be changed by unscrewing a knurled nut 8 accessible from the outside, depending on the type of turbine to be cleaned. The nose is retightened by turning the knurled nut in the opposite direction.

When the nose 4, 5, 6 is intended to receive an air apparatus (turbine), driving is effected by the passage of air with the aid of a specific connector known per se.

Figure 2:
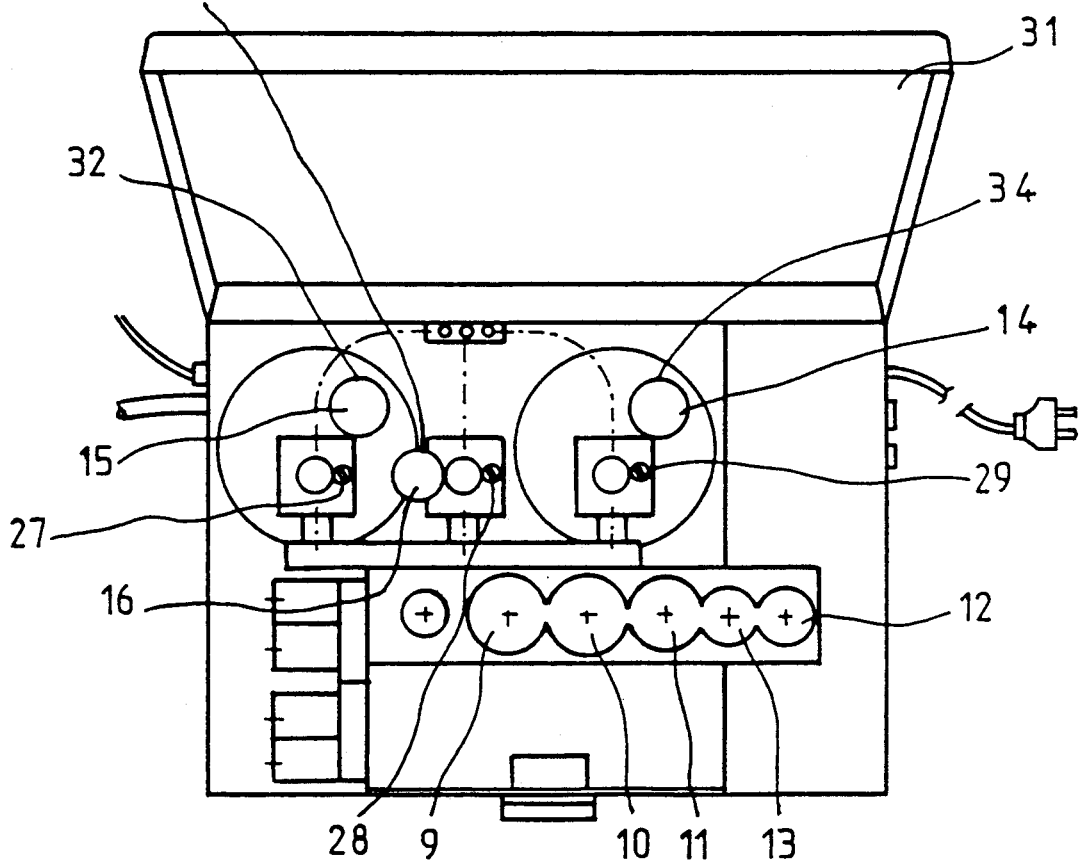
FIG. 2 is a view from above of the apparatus according to the invention, with the protective lid raised.

The motor noses are equipped in conventional manner with a shaft and driver, the respective shafts each being driven rotationally by a pinion 9, 10, 11 visible in FIG. 2, these pinions meshing with one another. A drive pinion 12 driven by an air motor (not shown) powers the whole arrangement, optionally with the aid of an intermediate satellite pinion (13).

A kinematic system simultaneously driving the noses and consequently the internal components of the parts fixed on them has been described above, because the cleaning operations must necessarily be carried out on moving components if they are to be effective.

The different fluids must now be passed through the parts.

The apparatus according to the invention comprises:
a water reservoir 14;

a reservoir 15 for disinfectant products in liquid or vapor form;

an oil reservoir 16.

The apparatus receives air under pressure by way of a pipe 30 provided with an adjustable pressure reducing valve 17 with a pressure gauge 18. Via a set of solenoid valves the air arrives in each of the reservoirs in an adjustable rhythm and in an adjustable cycle. This arrangement will be described later on.

The air thus admitted expels the fluids from their respective reservoirs into each of the noses. A safety valve closes the inlet on the nose if no handpiece is connected on the latter; when a handpiece is mounted on a nose the rear of the latter lifts the valve and frees the opening to admit fluid into the rear socket of the handpiece.

After passing through the parts which are to be cleaned the fluids enter the chamber 2 by way of the head of the handpiece and are discharged through a tube 19.

The solenoid valves are controlled in known manner by an electronic circuit board, the whole arrangement being supplied with electricity by way of a cable 20.

The various successive functions can be displayed on the front face on a panel 21. On this panel are disposed indicator lamps 22 indicating the cycle taking place and cycle time adjustment indicators 23.

The current is switched on with the aid of a main switch 24, while the cleaning cycle is started by means of a pushbutton 25.

A safety means ensures that the cleaning cycle can only start if the door 3 is closed, the opening of the door breaking the circuit.

Another safety means ensures that when the level of a liquid is insufficient a level warning light 26 lights up or is extinguished, interrupting the cycle which is proceeding.

Metering of the fluids is effected for each reservoir by means of a screw 27, 28, 29; adjustment can be made only during periods of utilization of these liquids. The reservoirs are closed by filler stoppers 32, 33, 34.

For a given metering adjustment the flow in respect of each liquid is automatically adapted in accordance with the number of noses used.

The apparatus requires only little maintenance and the various servicing interventions required can be carried out after raising the lid 31 or from the rear of the apparatus.

By way of example, time adjustments can be made within the following ranges and for the following functions:

washing: 18 to 100 seconds.
drying: 35 to 120 seconds, with the option of pulsated or non-pulsated dry air.
disinfectant: 18 to 100 seconds.
pause: 35 to 120 seconds.
drying: 18 to 100 seconds.
lubrication: 27 to 50 seconds.
extraction of products: 5 to 25 seconds.

An end of cycle indicator light indicates that the cycle is finished and that the parts are ready to be sterilized.

For the door 3 a sealing device in the form of a hollow tube 35 disposed around the frame receiving the door will advantageously be provided. When the door is closed and the apparatus is operated the tube 35 is placed under pressure. Because of the resulting inflation of the tube perfect tightness is achieved, since through the action of the pressure the flexible tube adapts itself perfectly to the contour shapes of the door and frame.

This sealing device is exempt from the leaktightness defects of conventional rubber seals resulting from ageing.

In addition, it makes it possible to obtain optimum leak tightness despite the slight positive pressures that may occur in the cleaning chamber during the operation of the apparatus.

The pneumatic operation of the apparatus will now be described with reference to the diagram shown in FIG. 4.

The different reservoirs 14, 15, 16 mentioned above are shown in that figure.

The system operates with air under pressure with the aid of inlets P, which with the aid of a set of solenoid valves delivers the air under pressure into the selected fluid reservoir corresponding to the working phase of the apparatus. The fluid is then expelled from the reservoir and is injected into the handpiece or handpieces or the turbine via the nose on which those parts are mounted.

The reservoirs 14, 15 will advantageously be provided with a device 36, 37 generating a mist of air and fluid enabling the metering of fluid to be adjusted.

Each nose receiving an instrument has associated with it a solenoid valve 38, 39, 40, 41 permitting or preventing the passage of the mist of water or disinfectant, the inlet of each of these solenoid valves being connected at a junction point 42, 43 to which both the water mist pipe 44 and the disinfectant mist pipe 45 lead.

In addition, each nose has associated with it an oil inlet 46, 47, 48, 49 situated downstream of the solenoid valve associated with said nose.

The oil distribution device 50 will for example consist of a known means injecting oil simultaneously into all the oil inlets.

As an alternative, the device will for example comprise a control unit which for the phases of the passage of water mist, disinfectant mist or oil provides an open-close mode for the solenoid valves associated with the noses by means of a sequential process.

With regard to the structure of the noses, provision will be made for these to have no seals, so that the washing and disinfection of the tips and spray tubes of the handpieces will be effected by overflowing.

Finally, provision will be made for the oil pipes to lead to the handpiece at a level below the inlet of the spray channels of the said handpiece, or the corresponding inlets in the nose supporting the handpiece, so that oil will be prevented from penetrating into the spray channels.

We claim:

1. Automatic apparatus for cleaning one or more dental handpieces or turbines, comprising a housing having a compartment for receiving handpieces or turbines to be cleaned, said compartment having a hinged door, a plurality of dental motor noses projecting downwardly from a top of said compartment so as to receive dental handpieces or turbines to be cleaned, said noses being equipped with an internal shaft and driver, means for driving said shafts of said motor noses in rotation, fluid reservoirs in said housing comprising a water reservoir, a reservoir for a disinfectant fluid and a lubricant fluid reservoir, a source of air under pressure, supply lines connecting said source of air to said fluid reservoirs and connecting said reservoirs to said motor noses, solenoid valves positioned in said supply lines so as to control the transmission of the pressurized air to said reservoirs in predetermined timed sequence to propel the respective fluids through each of said supply lines and through said motor noses so that dental handpieces or turbines positioned thereon having internal shafts will be rotated by said shafts of said motor noses while fluids are passed through said handpieces, and further comprising a safety valve on said supply line of each of said motor noses to shut off said supply line of a motor nose when no handpiece is positioned thereon.

2. Apparatus according to claim 1, in which said means for driving said shafts of said motor noses comprises pinions on said motor shafts, said pinions meshing with one another, a single drive pinion positioned and arranged to drive said meshing pinions and an air motor means for driving said single pinion.

3. Apparatus according to claim 1, further comprising a turbine nose projecting downwardly from said top of said compartment for cleaning a turbine, said turbine nose being held in place by a knurled nut positioned so as to be accessible from outside said housing.

4. Apparatus according to claim 1, in which each of said reservoirs is provided with a metering screw.

5. Apparatus according to claim 1, further comprising a seal for said door, said seal comprising a tube which is disposed around a frame receiving said door and is capable of being placed under pressure.

6. Apparatus according to claim 1, in which each of said reservoirs is provided with means for generating a mist of air and fluid enabling the metering of fluid to be adjusted.

7. Apparatus according to claim 1, in which said supply lines connecting said reservoirs with said motor noses comprises a common junction to which supply lines from said reservoir lead and branch lines connecting said junction with respective motor noses and in which there is a solenoid valve in each of said branch lines.

8. Apparatus according to claim 7, in which each of said branch lines has an oil inlet situated between said branch line solenoid valve and said motor nose.

* * * * *